(12) United States Patent
Lee et al.

(10) Patent No.: US 10,596,375 B2
(45) Date of Patent: Mar. 24, 2020

(54) COCHLEAR IMPLANT DEVICE AND STIMULATING METHOD THEREOF

(71) Applicant: NATIONAL CHIAO TUNG UNIVERSITY, Hsinchu (TW)

(72) Inventors: Chia-Fone Lee, Hsinchu (TW);
Yuan-Fang Chou, New Taipei (TW);
Chung-Yu Wu, New Taipei (TW);
Ming-Dou Ker, Zhubei (TW);
Chung-Chih Hung, Hsinchu (TW);
Xin-Hong Qian, Chiayi (TW)

(73) Assignee: National Chiao Tung University, Hsinchu (TW)

( * ) Notice: Subject to any disclaimer, the term of this patent is extended or adjusted under 35 U.S.C. 154(b) by 0 days.

(21) Appl. No.: 15/680,921

(22) Filed: Aug. 18, 2017

(65) Prior Publication Data
US 2018/0304077 A1   Oct. 25, 2018

(30) Foreign Application Priority Data

Apr. 21, 2017 (TW) .............................. 106113521 A (51) Int. Cl.
*A61N 1/36* (2006.01)
*A61N 1/372* (2006.01)
*H04R 25/00* (2006.01)
*A61N 1/05* (2006.01)

(52) U.S. Cl.
CPC ..... *A61N 1/36038* (2017.08); *A61N 1/37229* (2013.01); *H04R 25/554* (2013.01); *H04R 25/606* (2013.01); *A61N 1/0541* (2013.01); *H04R 2225/67* (2013.01)

(58) Field of Classification Search
CPC ............ A61N 1/36038; A61N 1/37229; A61N 1/0541; H04R 25/554; H04R 25/606; H04R 2225/67
See application file for complete search history.

(56) References Cited

U.S. PATENT DOCUMENTS

| | | | |
|---|---|---|---|
| 4,419,995 A | 12/1983 | Hochmair et al. | |
| 5,095,904 A | 3/1992 | Seligman et al. | |
| 5,653,742 A * | 8/1997 | Parker | A61D 7/00 607/116 |
| 6,549,814 B1 | 4/2003 | Strutz et al. | |

(Continued)

OTHER PUBLICATIONS

Fan-Gang Zeng et al., "Cochlear Implants: System Design, Integration, and Evaluation," IEEE Reviews in Biomedical Engineering, vol. 1, 2008, pp. 115-142.

*Primary Examiner* — Catherine M Voorhees
(74) *Attorney, Agent, or Firm* — Muncy, Geissler, Olds & Lowe, P.C.

(57) ABSTRACT

A cochlear implant device comprises a receiver, a processing device, a first electrode and a second electrode. The receiver is configured to receive outside voice signal. The processing device is coupled to the receiver, configured to receive and transfer the voice signal to an electrical stimulation signal. The first electrode connects to the processing device, disposed on stapes footplate ligament or oval window. The second electrode connects to the processing device, disposed on round window. Wherein the electrical stimulation signal is applied to stapes footplate ligament, oval window or round window to stimulate acoustic nerve through the first electrode or the second electrode.

8 Claims, 9 Drawing Sheets

Single    Different (56) References Cited

U.S. PATENT DOCUMENTS

| | | |
|---|---|---|
| 6,754,537 B1 | 6/2004 | Harrison et al. |
| 7,167,754 B1 | 1/2007 | Peeters et al. |
| 7,194,314 B1 * | 3/2007 | Richter .............. A61N 1/36036 |
| | | 600/25 |
| 7,317,944 B1 | 1/2008 | Overstreet |
| 7,966,077 B2 | 6/2011 | Risi |
| 8,082,040 B2 * | 12/2011 | Ibrahim ................ A61N 1/0541 |
| | | 607/115 |
| 2004/0133250 A1 * | 7/2004 | Ball ..................... A61N 1/0541 |
| | | 607/57 |
| 2006/0015155 A1 * | 1/2006 | Charvin .............. H04R 25/606 |
| | | 607/57 |
| 2006/0025833 A1 | 2/2006 | Daly |
| 2007/0005117 A1 * | 1/2007 | Fritsch ................ A61N 1/0541 |
| | | 607/56 |
| 2007/0021804 A1 | 1/2007 | Maltan et al. |
| 2007/0282397 A1 | 12/2007 | Ball |
| 2009/0118795 A1 | 5/2009 | Ibrahim et al. |
| 2011/0295331 A1 * | 12/2011 | Wells .................. A61N 5/0601 |
| | | 607/3 |
| 2011/0301681 A1 | 12/2011 | Risi |

\* cited by examiner

COCHLEAR IMPLANT DEVICE AND STIMULATING METHOD THEREOF

BACKGROUND OF THE INVENTION

1. Field of the Invention

The present invention relates to a cochlear implant device and stimulating method thereof, especially a minimally invasive cochlear implant device and stimulating method thereof.

2. Description of the Prior Art

The hearing-impaired, whose hair cells are damaged or do not completely developed, but usually have partial nerve fibers which do not completely lose their function. A cochlear implant device could be utilized to replace those hair cells. The cochlear implant device directly stimulates the normal nerve fibers so that the hearing could be transmitted to brain through the normal nerve fibers.

Therefore, the hearing aids like cochlear implant devices are researched and developed. Traditional cochlear implant devices usually have surgical implant units, electrodes, connecting wires, transmitting coils, and an outside speech device. However, the electrodes must be implanted into the cochlea. The surgery is complicated and has high risk. In addition, the cost is also very expensive.

SUMMARY OF THE INVENTION

One aspect of the present invention provides a cochlear implant device. The electrode of the cochlear implant device is disposed on the outside of the cochlea so that the risk of the surgery can be reduced. In addition, the structure is simple so that the cost will also be reduced.

The cochlear implant device comprises a receiver, a processing device, a first electrode and a second electrode. The receiver is configured to receive outside voice signal. The processing device is coupled to the receiver, configured to receive and transfer the voice signal to an electrical stimulation signal. The first electrode connects to the processing device, disposed on stapes footplate ligament or oval window. The second electrode connects to the processing device, disposed on round window. Wherein the electrical stimulation signal is applied to stapes footplate ligament, oval window or round window to stimulate acoustic nerve through the first electrode or the second electrode.

Another aspect of the present invention provides a stimulating method. The electrode of the cochlear implant device is disposed on the outside of the cochlea so that the risk of the surgery can be reduced. In addition, the structure is simple so that the cost will also be reduced.

The stimulating method comprises the following steps: (S1) a receiver receives outside voice signal; (S2) a processor receives and transfers the voice signal to an electrical stimulation signal; and (S3) a stimulating electrode receives the electrical stimulation signal and applies it to stapes footplate ligament, oval window or round window, to stimulate acoustic nerve.

Another aspect of the present invention provides a cochlear implant device. The electrode of the cochlear implant device is disposed on the outside of the cochlea so that the risk of the surgery can be reduced. In addition, the structure is simple so that the cost will also be reduced.

The cochlear implant device comprises a receiver, a processing device, two first electrodes and a second electrode. The receiver is configured to receive outside voice signal. The processor is coupled to the receiver, configured to receive and transfer the voice signal to an electrical stimulation signal. The two first electrodes connect to the processor, disposed on bone surface of the cochlea, configured to receive the electrical stimulation signal and separately apply different polar electrical signals to the cochlear bone. The second electrode connects to the processor, disposed on round window, configured to be a counter electrode.

Another aspect of the present invention provides a stimulating method. The electrode of the cochlear implant device is disposed on the outside of the cochlea so that the risk of the surgery can be reduced. In addition, the structure is simple so that the cost will also be reduced.

The stimulating method comprises the following steps: (S11) a receiver receives outside voice signal; (S12) a processor receives and transfers the voice signal to an electrical stimulation signal; and (S13) two stimulating electrodes receive the electrical stimulation signal and separately apply different polar electrical signals to the bone surface of the cochlea to stimulate acoustic nerve.

Compared to the prior art, the present invention provides a simple electrode structure and a minimally invasive manner for the cochlea. Besides it can effectively stimulate acoustic nerve, it can reduce the risk of the surgery and the cost.

DETAILED DESCRIPTION OF THE PREFERRED EMBODIMENT

Figure 1A:
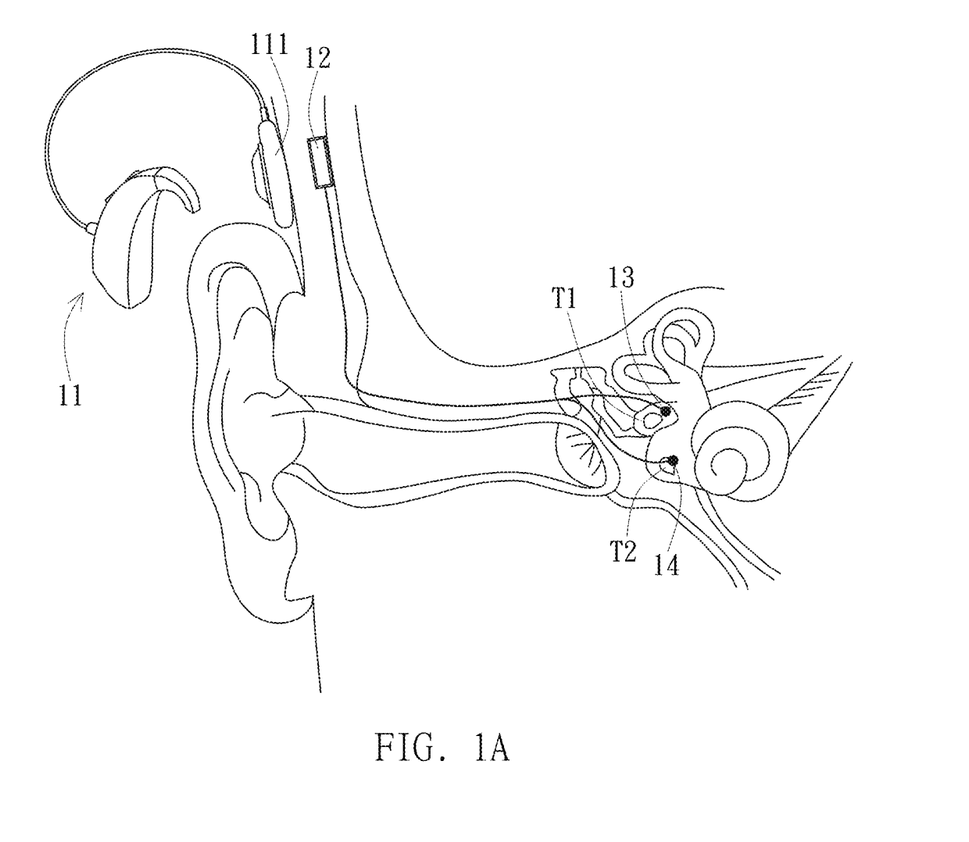
FIG. 1A is a schematic diagram of a cochlear implant device in the present invention.
Figure 1B:
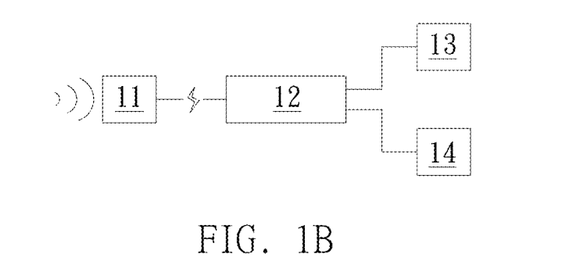
FIG. 1B is a block diagram of the embodiment of FIG. 1A.
Figure 1C:
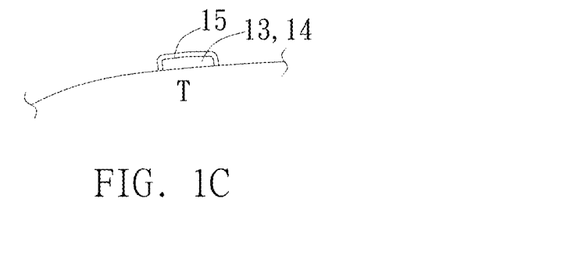
FIG. 1C is a side view diagram of one electrode in the present invention.

Please refer to FIG. 1A, FIG. 1B and FIG. 1C. A cochlear implant device preferably comprises a receiver 11, a processor 12, a first electrode 13 and a second electrode 14. The receiver 11 may be microphone or other speech processing devices. The receiver 11 is configured to receive outside voice signal, and then transfer the outside voice signal into wireless signal which is suitable for transmitting. The receiver 11 is like a normal hearing aid which could be hung on the ear, but not limited thereto.

The receiver 11 preferably comprises a processing unit (not shown) to transfer/encode voice signal into digital signal. In addition, the receiver 11 preferably connects to a sending coil 111 for transmitting the encoded voice signal through radio wave, but not limited thereto. In this embodiment, when the voice signal is transmitted by the receiver 11, it is already transferred into a wireless signal. The sending coil 111 may be attached to the skin of the head near the auricle, but not limited thereto.

The processor 12 is preferably disposed on the mastoid bone, but not limited thereto. It preferably comprises a receiving coil, a processing unit, and a stimulator. The processor 12 receives the voice signal (wireless signal) from the receiver 11 through the receiving coil; then the processing unit receives the voice signal (wireless signal) and transfers/decodes it into an electrical stimulation signal. The electrical stimulation signal can be transmitted to the first electrode 13 or the second electrode 14 by the stimulator.

In this embodiment, the first electrode 13 connects to the processor 12 and is disposed on the stapes footplate ligament T1. In detail, the first electrode 13 may be formed as a needle or a cylinder, and inserted into the stapes footplate ligament T1 for a better stability. The inserted depth is better to not penetrate through the ligament tissue. That is, the first electrode 13 does not penetrate to the next tissue to avoid damaging other tissues.

It is noted that the first electrode 13 may be formed as a planar electrode. Compared to the inserted type, the planar electrode can reduce the degree of invasion. In this circumstance, the first electrode 13 may be attached to the stapes footplate ligament T1 by biological glue (not shown) for a better stability. In addition, to avoid the rejection phenomenon between the first electrode 13 and other tissues inside the ear, a biocompatible layer 15 (e.g. polyimide or the like) may be used to cover the portion of the first electrode 13 does not contact with tissue T.

The second electrode 14 also connects to the processor 12 and is disposed on the round window T2. Similarly, the second electrode 14 is attached to T2 by biological glue. A biocompatible layer 15 may be used to cover the portion of the second electrode 14 does not contact with tissue T.

In this embodiment, the first electrode 13 is configured to be a stimulating (working) electrode, and the second electrode 14 is configured to a counter electrode. The first electrode 13 receives the electrical stimulation signal from the processor 12, and then applies it to the stapes footplate ligament T1. Accordingly, the electrical stimulation signal (e.g. current or voltage) is preferably transmitted between electrodes 13 and 14 in biphasic stimulating manner. While stimulating the acoustic nerve, it can eliminate the accumulated charge in single-phase (monophasic). It is noted that the minimum distance between the two electrodes cannot cause them conduct with each other. The electrical stimulation signal may be current or voltage. The current may supply a better stimulation. The stimulating manner is preferable biphasic, but not limited thereto.

Figure 1D:
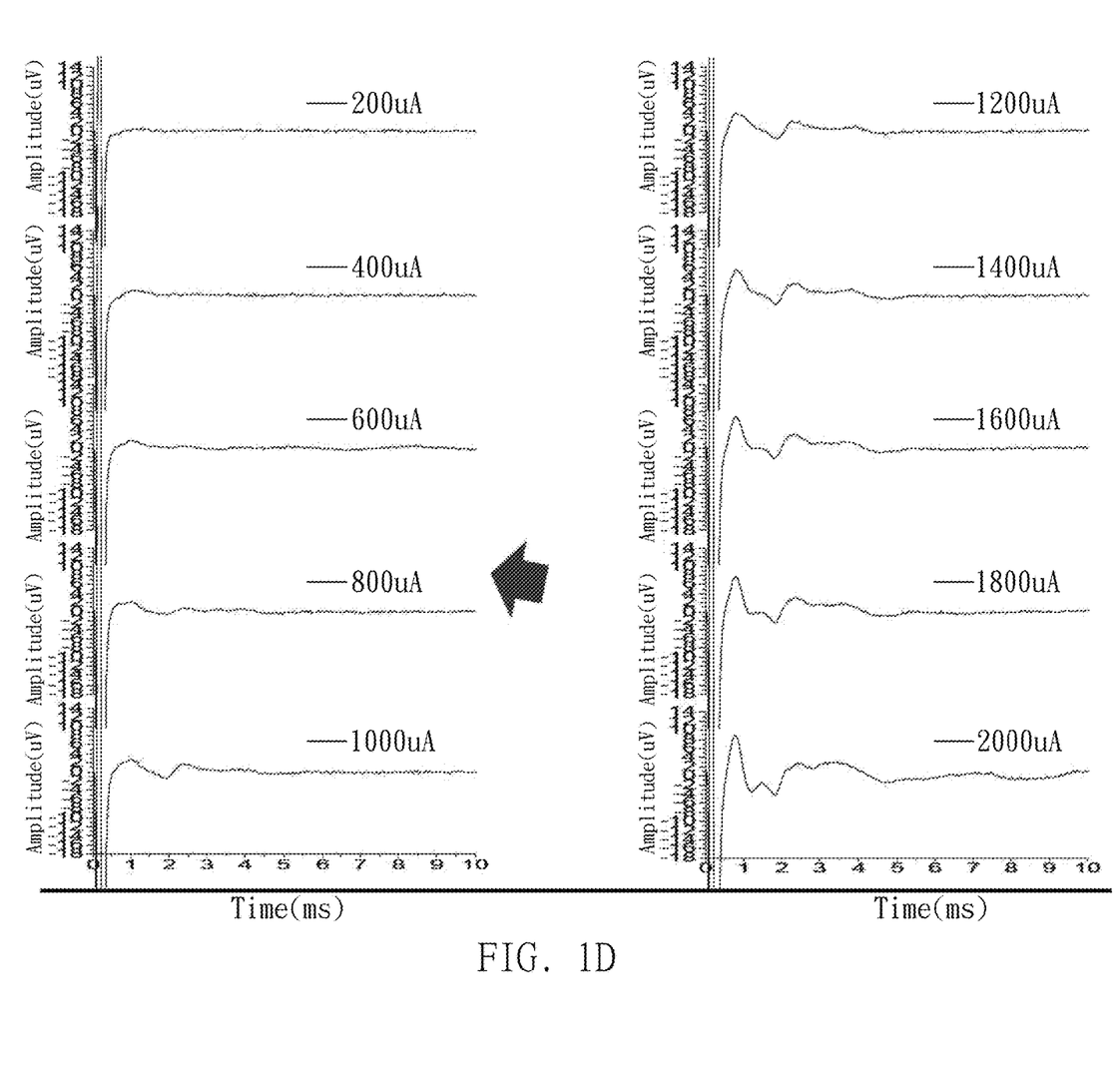
FIG. 1D is the electrical auditory brainstem response (EABR) measured waveform for the embodiment of FIG. 1A.

In the animal experiment, as shown in FIG. 1D, is an electrical evoked auditory brainstem response (EABR). A nerval action potential (pointed by the arrow) can be evoked when the current of the electrical stimulation signal reaches 800 µA. In detail, the determination is based on the fifth wave occurs. In this embodiment, the fifth wave occurs while the current reaches 800 µA.

Figure 2A:
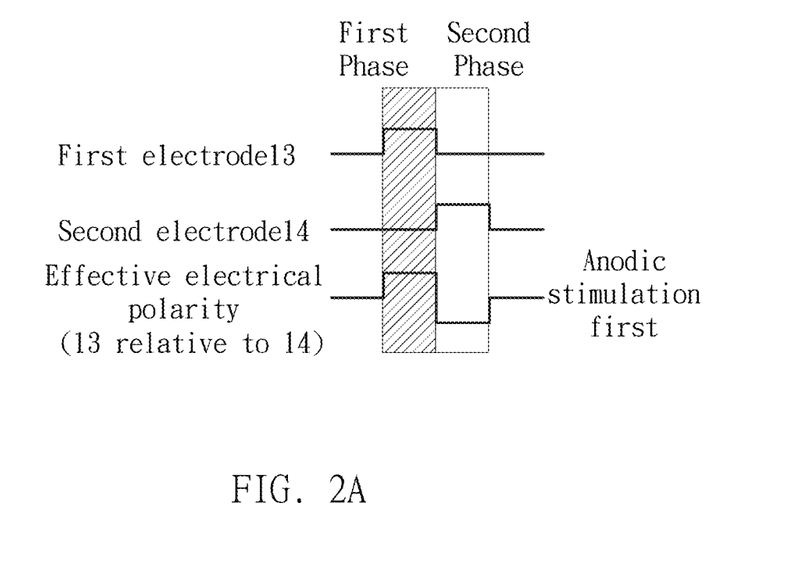
FIG. 2A and FIG. 2B are the electrical polarity (cathodic, anodic, or reference ground) on each electrode of a cochlear implant device in the present invention.
Figure 2B:
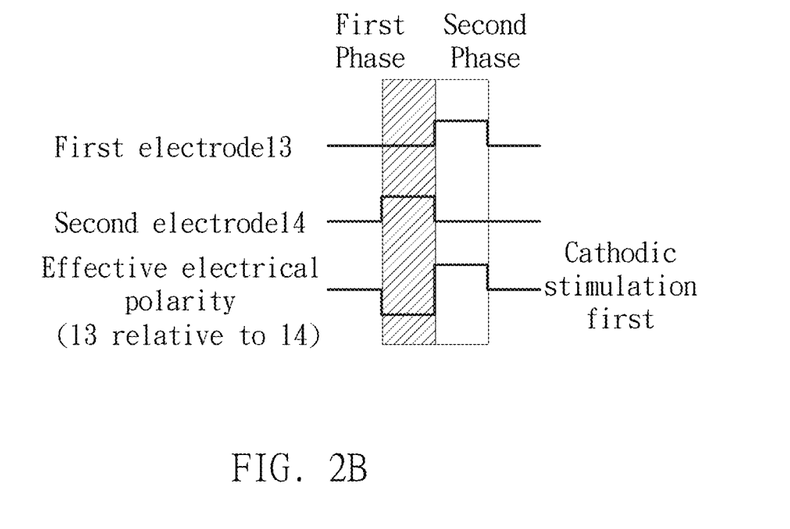
Figure 3A:
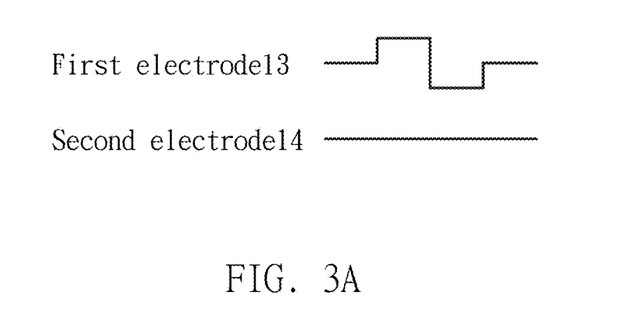
FIG. 3A~FIG. 3D are the another electrical polarity (cathodic, anodic, or reference ground) on each electrode of cochlear implant device in the present invention.
Figure 3B:
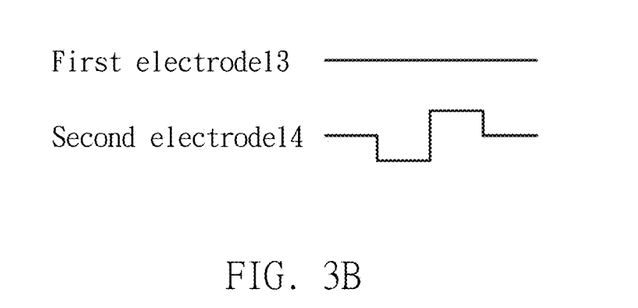
Figure 3C:
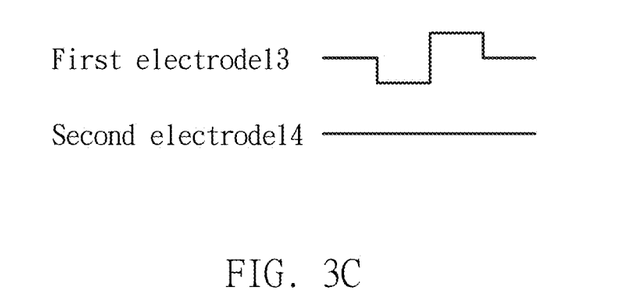
Figure 3D:
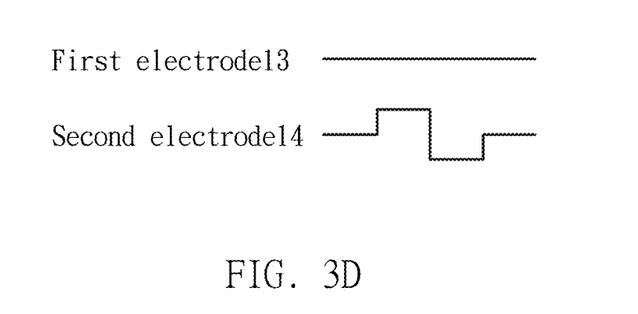

However, in other embodiments, the first electrode 13 and the second electrode 14 may be interchanged. For example, when the first electrode 13 is a working electrode, the second electrode 14 is a counter electrode. Conversely, when the second electrode 14 is a working electrode, the first electrode 13 is a counter electrode. It is noted that, in the common biphasic stimulating manner, it can be divided into two categories. The first category, during a complete stimulation, each of the two electrodes stimulates half time respectively. As shown in FIG. 2A and FIG. 2B, when the first electrode 13 as a working electrode in first half stimulation, the second electrode 14 is configured to be a counter electrode. When the second electrode 14 as a working electrode in second half stimulation, the first electrode 13 is configured to be a counter electrode. The difference is that in an equivalent stimulation in FIG. 2A, the stimulation is first to positive and second to negative. Due to the stimulation is negative polarity in the end, the corresponding voltage is a negative voltage. Accordingly, the biological reaction is a positive voltage is easy to be observed. In FIG. 2B, the equivalent stimulation is first to negative and second to positive. It has a much safer stimulation.

The second category, during a complete stimulation, the first electrode 13 and the second electrode 14 do not interchange. As shown in FIG. 3A~FIG. 3D, when the first electrode 13 as a working electrode, it supplies positive stimulation and negative stimulation, and the second electrode 14 is only configured to be a counter electrode. Conversely, when the second electrode 14 as a working electrode, it supplies positive stimulation and negative stimulation, and the first electrode 13 is only configured to be a counter electrode.

In the first category, each of the two electrodes stimulates half time respectively so that the cost of the negative voltage or current of the stimulator may be saved. In the second category, anyone of the two electrodes may be designated to be a reference bias.

It is noted that, the first electrode 13 and the second electrode 14 may be formed as a circle, a rectangle, a cylinder, a pyramid, or a needle. There is no specific restriction.

Figure 4:
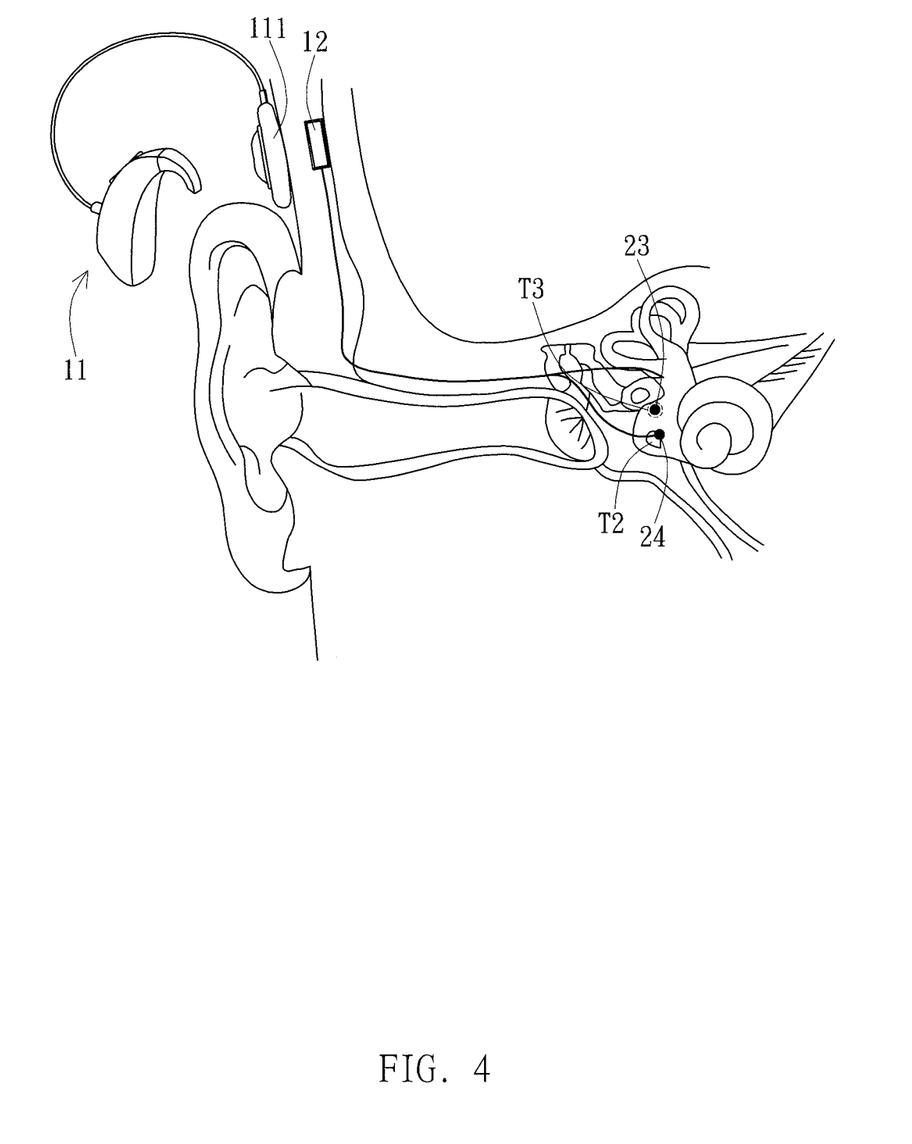
FIG. 4 is a schematic diagram of another stimulating method for cochlear implant device in the present invention.

In another embodiment, please refer to FIG. 4. The main structure is similar to the above embodiment. In this embodiment, the first electrode 23 is disposed on the oval window T3, and the second electrode 24 is still disposed on the round window T2. The first electrode 23 receives the electrical stimulation signal from the processor, and then applies it to the oval window T3 to stimulate the acoustic nerve. It is noted that both two ways can cure the tinnitus, however, the location of stapes footplate ligament T1-round window T2 is much more easily effectively stimulated by inserting an inserted electrode into T1. The location of oval window T3-round window T2 is suitable for using a planar electrode for a minimally invasive way. The needle electrode is used to dispose on the stapes footplate ligament T1 and the planar electrode is used to dispose on the oval window T3, but not limited thereto.

Figure 5:
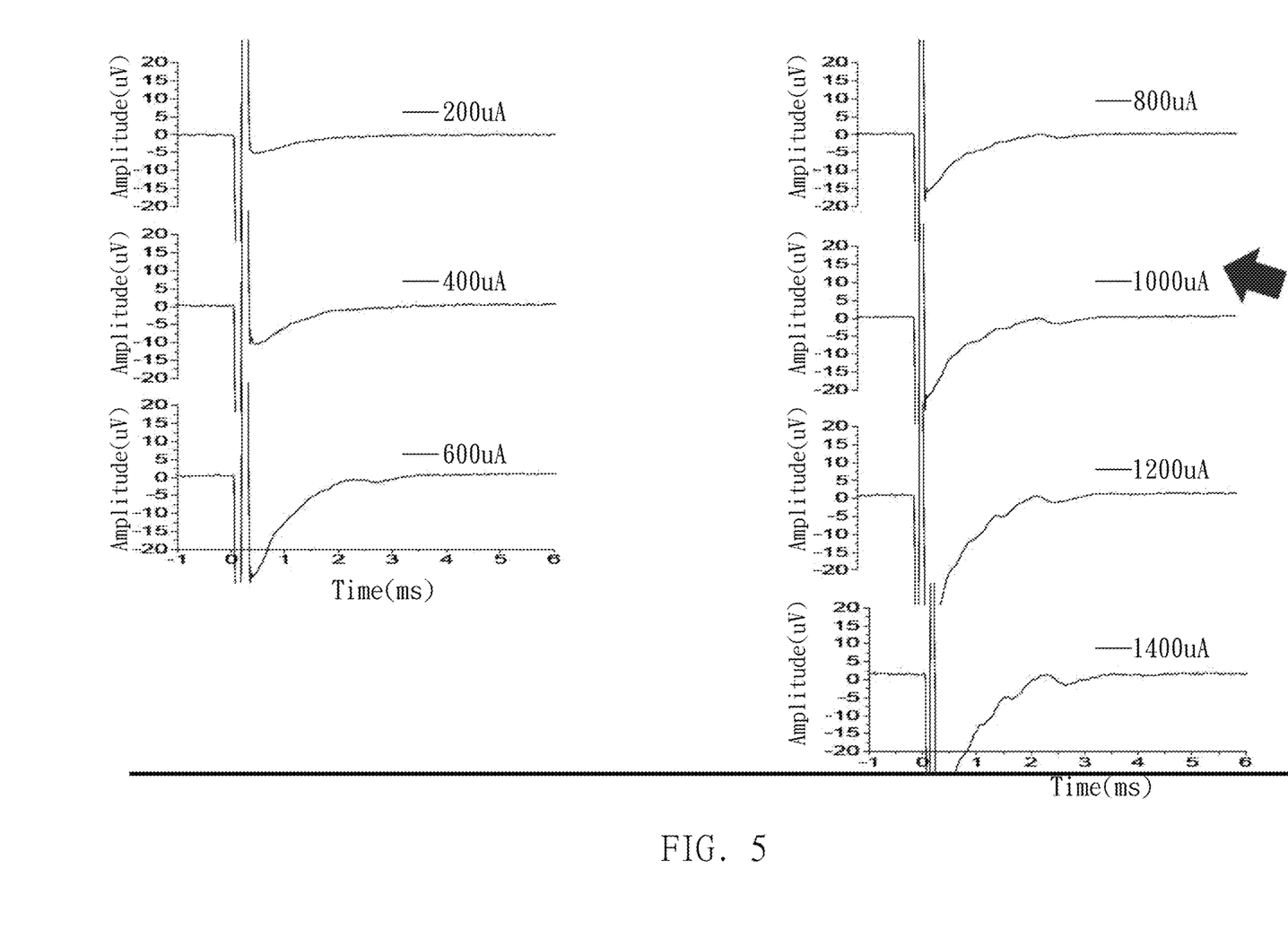
FIG. 5 is the electrical auditory brainstem response (EABR) measured waveform of another stimulating method for cochlear implant device in the present invention.

In another embodiment, the first electrode is disposed on the stapes, and the second is still disposed on the round window. In this embodiment, due to the first electrode is directly disposed on the bone, the first electrode is attached to the stapes through a bio-screw, but not limited thereto. The attached manner for the second electrode is similar to the above embodiment. As shown in FIG. 5, the data of the animal experiment shows that a nerval action potential (pointed by the arrow) can be evoked when the current of the electrical stimulation signal reaches 1000 µA.

In a preferable embodiment, the current of the electrical stimulation signal is set about 300~1000 μA to effectively evoke the nerval action potential. However, it is noted that the current value actually relates to the stimulating time. For example, in order to generate a current which could sufficiently evoke the nerval action potential, when the stimulating time is shorter, the needed current is larger. Conversely, when the stimulating time is longer, the needed current is smaller. Therefore, the current 300~1000 μA in this embodiment is only an example, not limited thereto. The upper limit of the electrical stimulation signal is preferable not to cause the adjacent tissue reactions.

Figure 6:
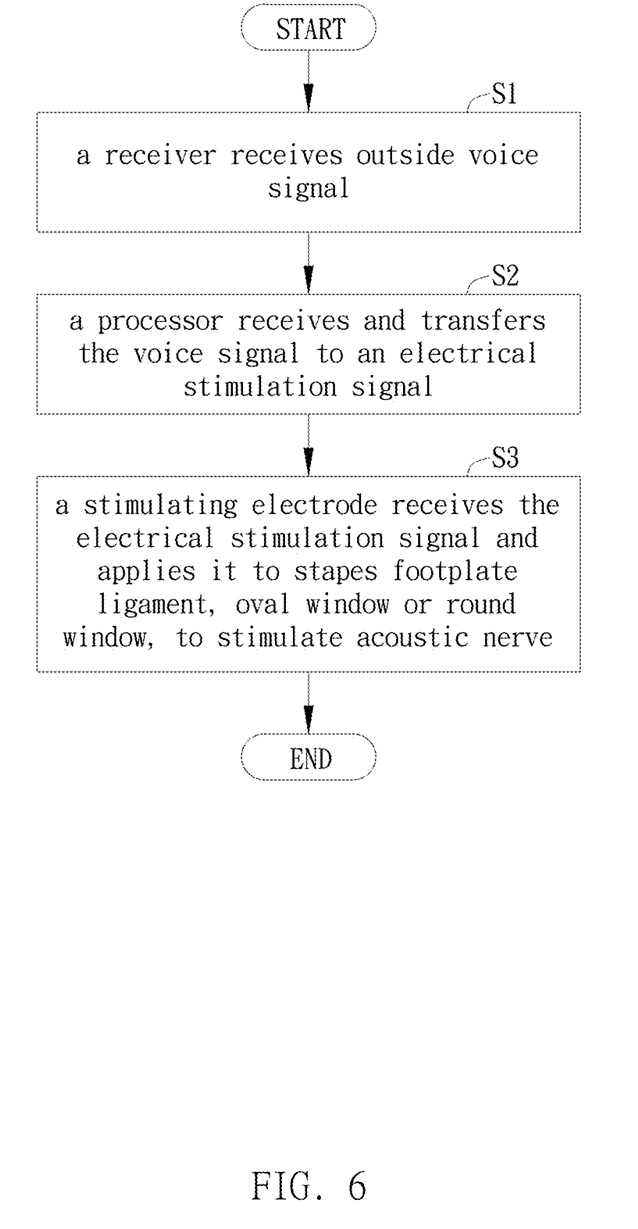
FIG. 6 is a flowchart of a stimulating method in the present invention.

Another embodiment in the present invention, as shown in FIG. 6. It is a stimulating method applied to the embodiment of FIG. 1A. The method comprises follow steps: (S1) a receiver receives outside voice signal; (S2) a processor receives and transfers the voice signal to an electrical stimulation signal; and (S3) a stimulating electrode receives the electrical stimulation signal and applies it to stapes footplate ligament, oval window or round window, to stimulate acoustic nerve.

The hardware structure for the stimulating method is described on the above embodiment, it is not discussed here.

Figure 7A:
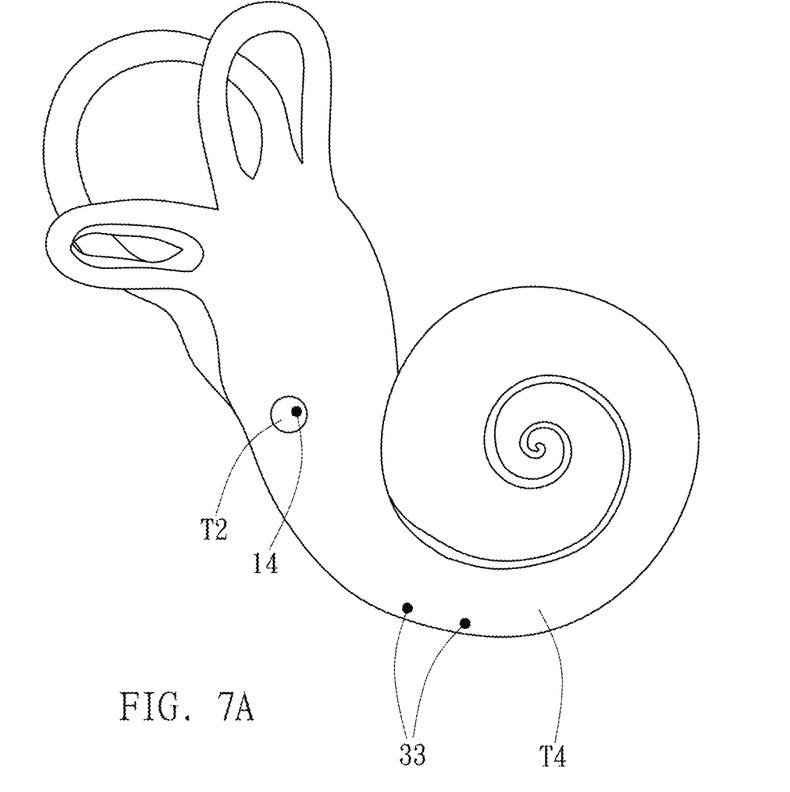
FIG. 7A and FIG. 7B are schematic diagrams of another stimulating method for cochlear implant device in the present invention.
Figure 7B:
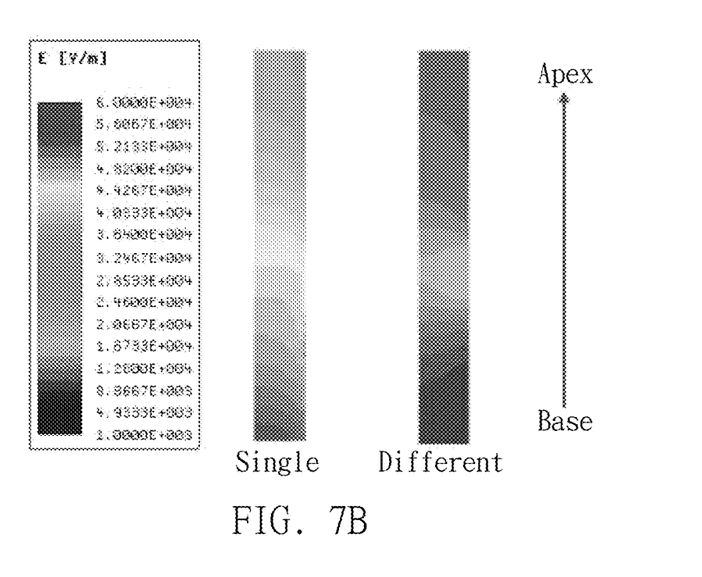

Another embodiment in the present invention, as shown in FIG. 7A and FIG. 7B. A cochlear implant device preferably comprises a receiver, a processor, two first electrodes 33 and a second electrode 14. Except for the location of the electrodes, other elements (not shown) are similar to the above embodiment.

The receiver is like a normal hearing aid which could be hung on the ear, but not limited thereto. The receiver preferably comprises a processing unit (not shown) to transfer/encode voice signal into digital signal. In addition, the receiver preferably connects to a sending coil for transmitting the encoded voice signal through radio wave, but not limited thereto. In this embodiment, when the voice signal is transmitted by the receiver, it is already transferred into a wireless signal. The sending coil may be attached to the skin of the head near the auricle, but not limited thereto.

The processor is preferably disposed on the mastoid bone, but not limited thereto. It preferably comprises a receiving coil, a processing unit, and a stimulator. The processor receives the voice signal (wireless signal) from the receiver through the receiving coil; then the processing unit receives the voice signal (wireless signal) and transfers/decodes it into an electrical stimulation signal. The electrical stimulation signal can be transmitted to the electrode by the stimulator.

In this embodiment, the two first electrodes 33 are configured to be stimulating electrodes. They both connect to the processor and disposed on the bone surface of the cochlea T4. The preferable position locates on the high-frequency area. Consider the basement of the cochlea is a high-frequency area, the electrodes 33 position may be the area where the acoustic frequency exceeds 1000 Hz. This way has an ability to compensate high frequency of hearing impair. Specifically, electrodes 33 can be disposed on the area where the frequency is 5000 Hz~15000 Hz. The 1000 Hz is used to be a boundary between reserving original low-frequency hearing (<1000 Hz) and the electrical stimulation. The second electrode also connects to the processor and is disposed on the round window T2, is configured to be a counter electrode.

The first electrodes 33 are disposed on the bone surface of the cochlea, preferably located on the high-frequency area for supplying high-frequency response electrical stimulation signal to avoid damaging the cochlea. The first electrodes 33 receive the electrical stimulation signal and separately apply different polar electrical signals to the cochlear bone. It is noted that, to separately apply different polar electrical signals, there are at least two first electrodes needed and a second electrode. However, in other embodiment, take four first electrodes and a second electrode as an example for a simulated test. As shown in FIG. 7B, if only one electrode is given the voltage signal (e.g. only one of the first electrodes supplies the electrical stimulation signal), the electrical field distribution can be obtained as shown (single). If different polar voltage signals are applied (e.g. four first electrodes respectively apply −2V, −2V, +10V and −1V) to the cochlear bone, the electrical field distribution can be obtained as shown (different). FIG. 7B shows the electrical field distribution of base (high-frequency area) through apex (low-frequency area) of the cochlea. The voltage values are only taken for an example, but not limited thereto.

By separately applying different polar electrical signals, it can accurately control the stimulating position. In practice by this way, the purpose is to limit the stimulating target on the specific area and eliminate the wrong stimulation on other areas.

It is noted that, the above embodiment arranges two and four first electrodes, however, when the process development is much more mature, the size of the electrode will be reduced. Therefore, in the same area the arranged electrode will increase. The minimum distance between each two electrodes cannot cause they conduct with each other.

In this embodiment, the portions where the first electrodes 33 and the second electrode 14 do not contact with T2 and T4 respectively, covered by biocompatible layers. Wherein the first electrodes 33 may be attached to the bone surface of the cochlea by bio-screws.

Figure 8:
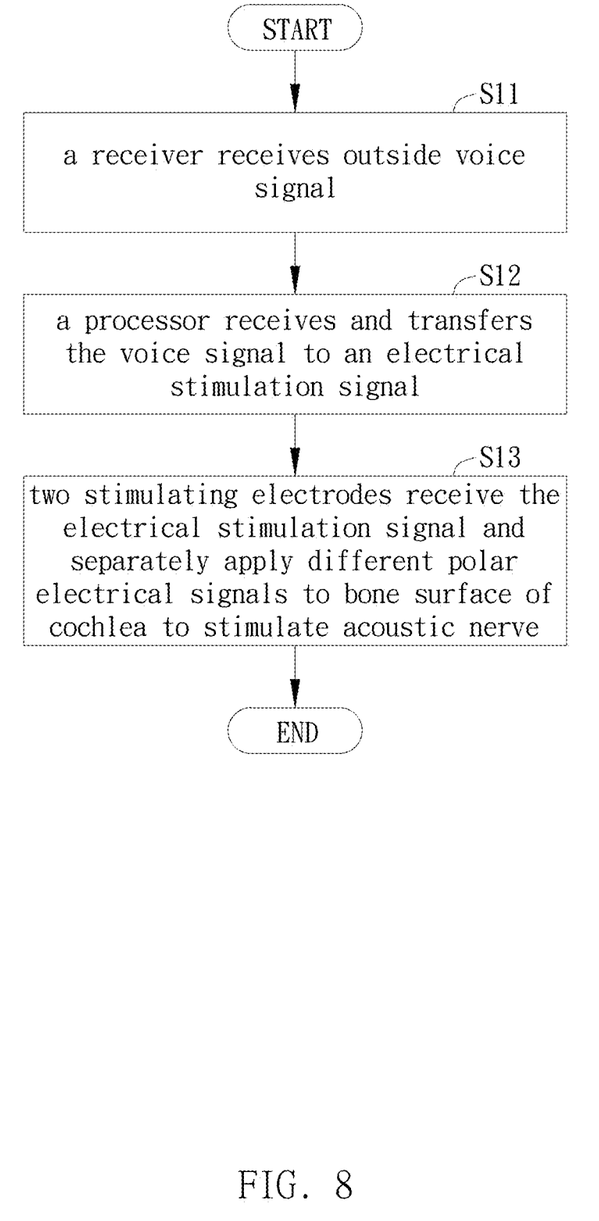
FIG. 8 is a flowchart of another stimulating method in the present invention.

Another embodiment in the present invention, as shown in FIG. 8. It is a stimulating method applied to the embodiment of FIG. 7. The method comprises follow steps: (S11) a receiver receives outside voice signal; (S12) a processor receives and transfers the voice signal to an electrical stimulation signal; and (S13) two stimulating electrodes receive the electrical stimulation signal and separately apply different polar electrical signals to the bone surface of the cochlea to stimulate acoustic nerve.

The hardware structure for the stimulating method is described on the above embodiment, it is not discussed here.

Compared to the prior art, the present invention provides a simple electrode structure and a minimally invasive manner for the cochlea. Besides it can effectively stimulate acoustic nerve, it can reduce the risk of the surgery and the cost.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A cochlear implant device for working in connection with a cochlea and a round window, comprising:
    a receiver, configured to receive an outside voice signal;
    a processor, coupled to the receiver and configured to receive and transfer the voice signal to an electrical stimulation signal;
    at least two first electrodes connected to the processor and configured to be disposed on a bone surface of a high-frequency area of the cochlea and outside the cochlea, wherein the at least two first electrodes are configured to receive the electrical stimulation signal and the processor is configured to apply different polar electrical signals to the bone surface of the cochlea; and a second electrode connected to the processor and configured to be disposed on the round window, wherein the second electrode is configured to be a counter electrode.

2. The device as claimed in claim 1, further comprising biocompatible layers, wherein the first electrodes and the second electrode are respectively partially covered by the biocompatible layers.

3. The device as claimed in claim 1, further comprising bio-screws, wherein the first electrodes and the second electrode are respectively adapted to be disposed on the bone surface of the cochlea by the bio-screws.

4. The device as claimed in claim 1, wherein the electrical stimulation signal is about 300~1000 µA.

5. A stimulating method for a cochlear implant device of claim 1, comprising:

receiving the outside voice signal by the receiver;

receiving and transferring the voice signal to the electrical stimulation signal from the receiver by the processor; and receiving the electrical stimulation signal from the processor and separately applying the different polar electrical signals to the bone surface of a high-frequency area of cochlea to stimulate acoustic nerve by the at least two first electrodes.

6. The method as claimed in claim 5, wherein the at least two first electrodes and the second electrode are adapted to be disposed on the bone surface of the cochlea by bio-screws.

7. The method as claimed in claim 5, wherein the at least two first electrodes and the second electrode are adapted to be partially covered by a biocompatible layer.

8. The device as claimed in claim 1, wherein a frequency range of the high-frequency area is exceed 1000 Hz.

* * * * *